United States Patent

Likibi

[11] Patent Number: 5,847,196
[45] Date of Patent: Dec. 8, 1998

[54] OXANILIDE U-V ABSORBERS

[75] Inventor: Parfait Jean Marie Likibi, Newburgh, Ind.

[73] Assignee: General Electric Company, Pittsfield, Mass.

[21] Appl. No.: 944,751

[22] Filed: Oct. 6, 1997

Related U.S. Application Data

[62] Division of Ser. No. 783,598, Jan. 13, 1997, Pat. No. 5,698,732.
[51] Int. Cl.$^6$ .................................................. C07C 261/00
[52] U.S. Cl. ................................................ 560/43; 560/39
[58] Field of Search ........................................ 560/43, 39

[56] References Cited

U.S. PATENT DOCUMENTS

| | | |
|---|---|---|
| 3,683,020 | 8/1972 | Luethi et al. ............................ 564/153 |
| 3,906,033 | 9/1975 | Biland et al. . |
| 3,989,672 | 11/1976 | Vestergaard . |
| 4,618,638 | 10/1986 | Dexter et al. . |
| 5,556,936 | 9/1996 | King, Jr. et al. . |
| 5,569,674 | 10/1996 | Yokoyama et al. . |

OTHER PUBLICATIONS

EP Search Report for European Equivalent Application No. EP 98 30 0209.

*Primary Examiner*—Gary Geist
*Assistant Examiner*—Brian J. Davis

[57] ABSTRACT

Oxalic acid diarylamides are described as useful monomers and comonomers in the polymerization of polycarbonates. The resin products resist degradation by ultra-violet light radiation. They can also be incorporated as comonomer or monomer in the polyester, polyester, polyether, polyethersulfone resins. They can also be used as UV stabilizers in the aforemetioned systems.

5 Claims, No Drawings

OXANILIDE U-V ABSORBERS

This is a divisional of application serial no. 08/783,598 filed on Jan. 13, 1997 now U.S. Pat. No. 5,698,732.

BACKGROUND OF THE INVENTION

1. Field of the Invention

The invention relates to oxalic acid diarylamides and more particularly to oxalic acid bis-hydroxydiarylamides and their use in absorbing ultra-violet light.

2. Brief Description of Related Art

Oxanildes based on benzene and substituted benzenes are known to be useful as ultra-violet light absorbing compounds; see for example the description given in U.S. Pat. No. 4,618,638. The patent describes these oxanildes as useful monomeric compounds for incorporation into a variety of polymer systems, including polycarbonates, to stabilize them against degradation by exposure to ultra-violet radiation.

In a similar vein, the U.S. Pat. No. 3,906,033 describes oxalic acid diarylamides which are useful as ultra-violet absorbing light compounds.

SUMMARY OF THE INVENTION

The invention comprises a compound of the formula:

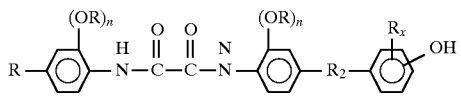
(I)

wherein n is an integer of 0 to 1; x is an integer of 0 to 4; R represents a monovalent moiety of the formula:

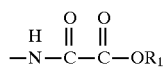
(II)

or

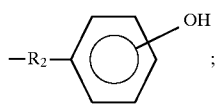
(III)

wherein $R_1$ is alkyl or aryl; and $R_2$ represents alkylene.

The term "alkyl" as used herein means the monovalent moiety obtained upon removal of a hydrogen atom from a parent alkane. Representative of alkyl are methyl, ethyl, propyl, butyl, pentyl, hexyl, heptyl, octyl, nonyl, undecyl, decyl and dodecyl. Preferred alkyl have from 1 to 12 carbon atoms, inclusive.

The term "alkylene" as used herein means the divalent moiety obtained on removal of two hydrogen atoms, each from a parent hydrocarbon alkane and include, for example, methylene, ethylene, propylene, butylene, pentylene, heptylene, octylene and isomeric or alicyclic forms thereof, preferably having from 1 to 8 carbon atoms.

The compounds of formula (I) described above wherein R represents the monovalent moiety of formula (II) are useful as intermediate compounds to prepare the compounds (I) wherein R represents the monovalent moiety of formula (III) and as chain stoppers in condensation polymerizations. The compounds of formula (I) given above wherein R is the monovalent moiety of formulas (III) is useful as an ultra-light absorbing compound to protect organic materials, more particularly polymers, copolymers and blends thereof from the deleterious effect of ultra-violet rays. Due to the presence of two independent hydroxyl groups, these compounds are conceptually similar to Bisphenol A. They can be used as monomer and comonomer in the preparation of polymers such as polycarbonates, polyesters, polyethersulfone, polyethers, polyurethanes and some coating components of acrylic and polyester enamels that are cross linked with hydroxymethyl-melamine and/or alkoxymethyl melamine curing agents. Furthermore, with their high molecular weight and their hydroxyl anchors, the compounds of the present invention are resistant to volatilization and exudation from resin compositions during processing and/or weathering.

The compound (I) of the invention, unlike aniline derivatives based oxanilide, absorb at higher wavelength without any detrimental effects on their absorbtivity. Contrary to derivatives of aminophenol, the formation of the oxanilide functionality does not affect the reactivity of the hydroxyl group, they are not in the same phenyl ring and are separated by an alkylene or alicyclic bridge.

DETAILED DESCRIPTION OF THE PREFERRED EMBODIMENTS OF THE INVENTION

The compounds (I) of the invention may be prepared by reaction of stoichiometric proportions of a hydroxyamino-diphenylalkane of the formula (IV) with a dialkyl oxalate (V) according to the schematic formula:

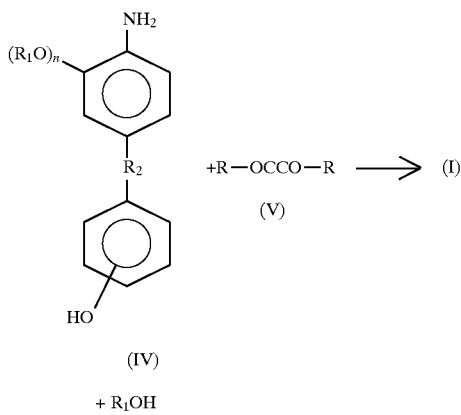

+ $R_1OH$

The compounds of formula (IV) are generally well known as are methods of their preparation; see for example the descriptions given in Offenlegungsschrift 29 45 179 and Auslegeschrift 1 251 334.

The compounds of formula (V) are also generally well known as are methods for their preparation. Representative of known compounds (V) are dimethyl oxalate, diethyl oxalate, dipropyl oxalate, dibutyl oxalate, dientyl oxalate oxalic acid, and oxalyl dichloride.

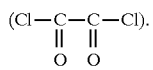

The reaction of the compounds (IV) with compounds (V) proceeds at reflux temperatures and ambient pressures in the presence of a lewis acid and an inert solvent. The term "inert solvent" as used herein means a solvent for the reactants which does not enter into or adversely affect the desired course of the reaction. Representative of inert solvents are benzene, toluene, cyclohexane; preferably halogenated aromatic solvents such as dichlorobenzene.

Upon completion of the reaction, the desired product (I) may be separated from the reaction mixture by conventional means such as distillation, precipitation and filtration.

Although not necessary, it may be advantageous to carry out the preparation of the compounds (I) of the invention under an inert atmosphere, such as a nitrogen gas blanket.

The invention will be better understood with reference to the following examples, which are presented for purposes of illustration rather than for limitation and set forth the best mode contemplated for carrying out the invention.

EXAMPLE 1

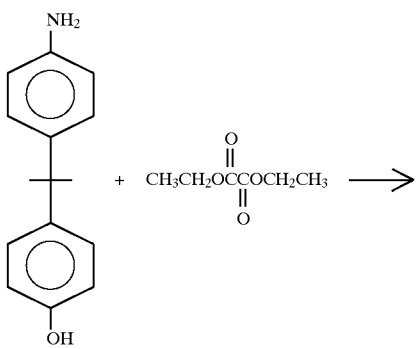

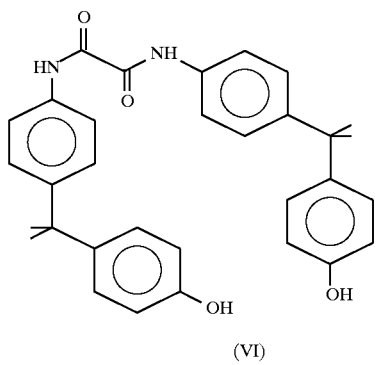

(VI)

A 3 liter round bottom flask equipped with an overhead stirrer, a condenser a Dean Stark trap and a thermometer was charged with:

113.64 grams of 2-(4-aminophenyl)-2-(4'-hydroxyphenyl) propane (0.5 mole);

36.53 grams of diethyl oxalate (0.25 mole);

20 grams of boric acid; and 600 ml of ortho dichlorobenzene.

The resulting mixture was heated to a temperature of 177° C. for 12 hours and refluxed at 185° C. for 6 hours. During the hold at 175° C., ethanol was collected in the trap. Afterward, the reaction mixture was allowed to cool to 120° C., then poured into an ice cooled solution of toluene. The product (VI) precipitated out. It was collected by filtration, washed with water and oven dried at 120° C. The product was recrystallized in toluene. MP: 234°–235° C. The structure was confirmed by $^1$H and $^{13}$C NMR. Yield: 80%.

EXAMPLE 2

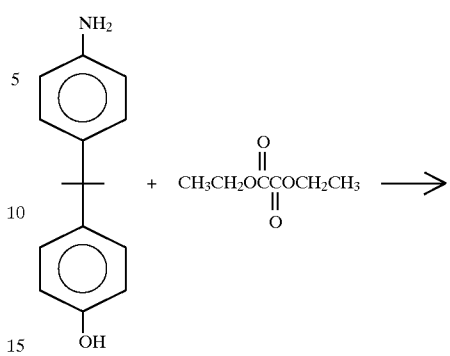

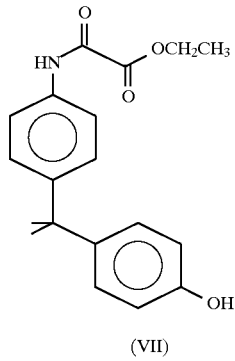

(VII)

A round bottom flask equipped with a condenser, a dean stark trap, an overhead stirrer and a thermometer was charged with:

700 grams of diethyl oxalate;

60 grams of boric acid; and 117 grams of 2,2-(4-aminophenyl)-(4'-hydroxyphenyl) propane.

The resulting mixture was heated and stirred at a temperature of 150° C. for 6 hours. After draining away, ethanol trapped in the Dean-Stark, the reaction mixture was refluxed for 6 hours at 185° C. Thereafter, nearly 400 ml of diethyl oxalate was distilled off. The remainder of the reaction mixture was allowed to cool to 120° C. and subsequently poured in an ice cooled beaker containing 1500 ml of toluene. The product (VII) precipitated out, was collected by filtration and was finally recrystallized from toluene. Spectroscopic data are consistent with the assigned structure (VII). Yield 95%.

EXAMPLE 3

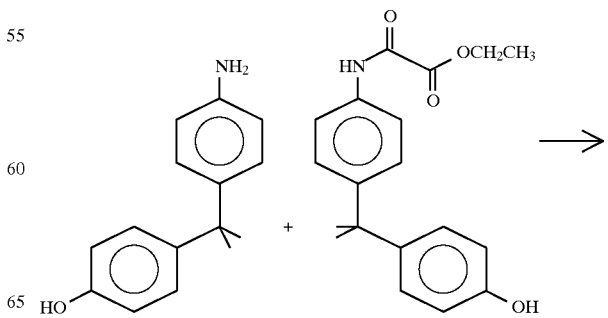

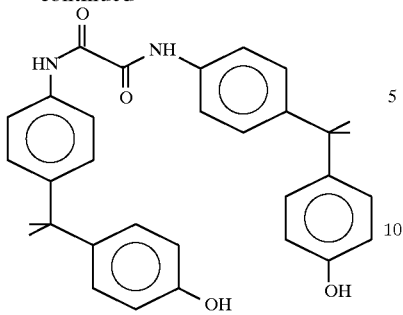

(VI)

A round bottom flask equipped with an overhead stirrer, a condenser, a Dean Stark trap and a thermometer was charged with:
- 500 ml of ortho dichlorobenzene;
- 20 grams of boric acid;
- 32.7 grams of the compound prepared in Example 2, supra.; and
- 23 grams of 2,2-(4-aminopheny)(4'-hydroxyphenyl) propane.

The resulting mixture, with stirring, was heated to a temperature 175° C. for 12 hours. After emptying the trap, the reaction mixture was refluxed at 185° C. for an additional 6 hours. Thereafter it was allowed to cool to 120° C. and poured in a cold solution of toluene. The product (VI) precipitated out, was collected by filtration and dried at 120° C. The product (VI) can also be recovered by cooling the reaction mixture at room temperature with vigorous stirring. Recrystallization from toluene afforded the pure product whose spectroscopic data are identical to those of the product prepared in Example 1, supra.

The compounds (I) of the invention absorb ultra-violet light within the region of from about 285 to 320 m$\mu$. They can be incorporated into polycarbonate polymer systems, replacing from 1 to 10 percent by weight of bisphenol-A, following the procedure for example of U.S. Pat. No. 3,989,672 to obtain polycarbonate resin resistant to degradation by exposure to ultra-violet light, or they can be added in the bulk of any other polymer as additives.

What is claimed:

1. A compound of the formula:

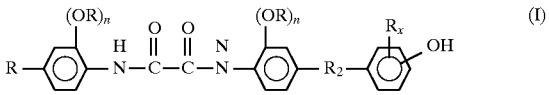

wherein n is an integer of 0 to 1; x is an integer of 0 to 4; represents a monovalent moiety of the formula:

or

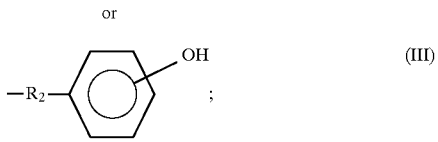

wherein $R_1$ is alkyl or aryl; and $R_2$ represents alkylene.

2. A compound according to claim 1 wherein R represents the moiety of formula (II).

3. A compound according to claim 1 wherein R represents the moiety of formula (III).

4. A compound according to claim 1 wherein n is O.

5. The compound of formula:

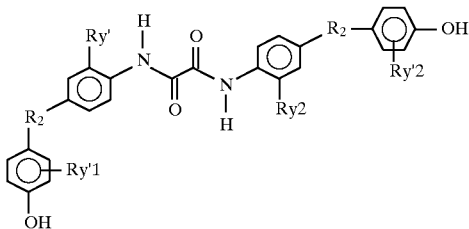

wherein $R_2$ represents alkylene; Ry1 and Ry2 represent alkyl, alkoxy or alkylaryl; and Ry'1 and Ry'2 represents Br, Cl, alkyl, alkoxy or alkyl aryl.

* * * * *